(12) United States Patent
Ram

(10) Patent No.: US 6,517,348 B1
(45) Date of Patent: Feb. 11, 2003

(54) DENTAL OSCILLATING CLEANING IMPLEMENT AND METHOD OF USING SAME

(76) Inventor: Zeev Ram, 10 Bustenai St., Rehovot 76289 (IL)

( * ) Notice: Subject to any disclaimer, the term of this patent is extended or adjusted under 35 U.S.C. 154(b) by 0 days.

(21) Appl. No.: 09/633,104

(22) Filed: Aug. 4, 2000

Related U.S. Application Data

(63) Continuation-in-part of application No. 09/240,857, filed on Feb. 1, 1999, now abandoned.

(30) Foreign Application Priority Data

Feb. 2, 1998 (IL) .................................................. 123160

(51) Int. Cl.⁷ ................................................ A61C 3/03
(52) U.S. Cl. ......................... 433/118; 433/82; 433/147
(58) Field of Search ............................ 433/80, 82, 118, 433/119, 147; 15/22.1, 24; 601/142; 606/161

(56) References Cited

U.S. PATENT DOCUMENTS

| | | | |
|---|---|---|---|
| 904,990 A | 11/1908 | Powers | 433/147 |
| 1,327,477 A | 1/1920 | Ivory | 433/147 |
| 3,133,351 A | 5/1964 | Von Seggern | 433/119 |
| 3,335,443 A | 8/1967 | Parisi et al. | 433/119 |
| 3,636,947 A | 1/1972 | Balamuth | 433/119 |
| 3,828,770 A | 8/1974 | Kuris et al. | 433/119 |
| 3,987,549 A | 10/1976 | Robertelli | 433/128 |
| 4,192,035 A | 3/1980 | Kuris | 15/22.1 |
| 4,333,197 A | 6/1982 | Kuris | 433/119 |
| 4,505,676 A | 3/1985 | Gonser | 433/119 |
| 4,576,190 A | 3/1986 | Youssef | 132/89 |
| 4,580,979 A | 4/1986 | Leonard | 433/118 |
| 4,735,200 A | 4/1988 | Westerman | 15/22 |
| 4,787,847 A | 11/1988 | Martin | 433/119 |
| 4,880,382 A | 11/1989 | Moret et al. | 433/118 |
| 4,903,688 A | 2/1990 | Bibby et al. | 433/80 |
| 4,991,249 A | 2/1991 | Suroff | 15/22.5 |
| 5,029,358 A | 7/1991 | Zimmerman | 15/167.1 |
| 5,123,841 A | 6/1992 | Milner | 433/125 |
| 5,165,131 A * | 11/1992 | Staar | 15/22.1 |
| 5,393,229 A | 2/1995 | Ram | 433/118 |
| 5,438,726 A * | 8/1995 | Leite | 15/105 |
| 5,573,020 A | 11/1996 | Robinson | 132/322 |
| 5,593,304 A | 1/1997 | Ram | 433/82 |
| 5,700,146 A | 12/1997 | Kucar | 433/118 |
| 5,709,233 A | 1/1998 | Boland et al. | 132/322 |
| 5,947,912 A * | 9/1999 | Montagnino | 433/118 |

FOREIGN PATENT DOCUMENTS

| | | |
|---|---|---|
| EP | 0 704 180 A1 | 5/1996 |
| JP | 8224259 | 9/1996 |
| WO | WO 98/36703 | 2/1998 |

\* cited by examiner

*Primary Examiner*—John J. Wilson
(74) *Attorney, Agent, or Firm*—Blank Rome Comisky & McCauley LLP

(57) ABSTRACT

A dental cleaning implement comprising: a handpiece graspable at one end by a user, an oscillating drive within the handpiece, a head located at the opposite end of the handpiece which includes a coupler for releasably attaching a toothpick or an interdental toothbrush thereto. The oscillating drive is adapted to provide oscillations of up to 15,000 strokes per second, preferably from 1 to 5,000 strokes per second, and the implement may optionally further comprise a selector for varying the frequency of oscillation.

4 Claims, 2 Drawing Sheets

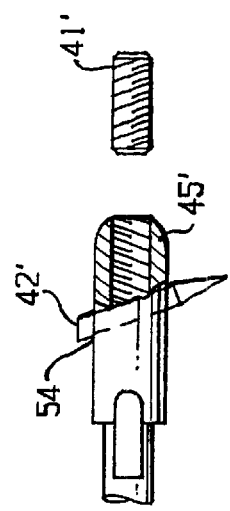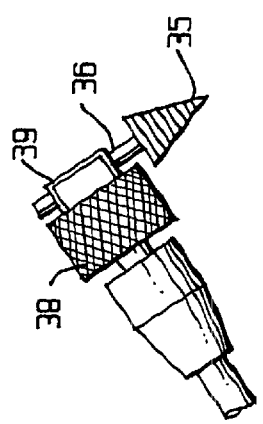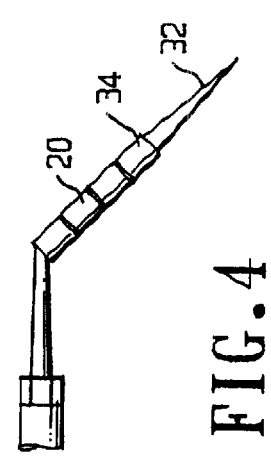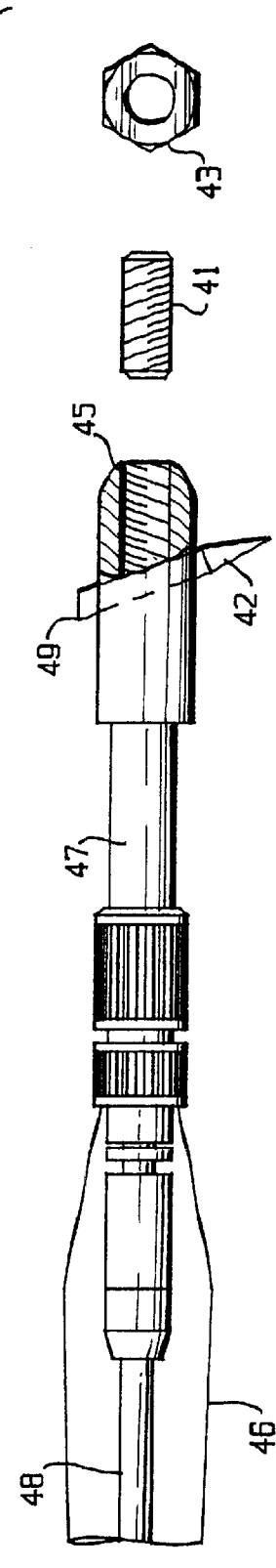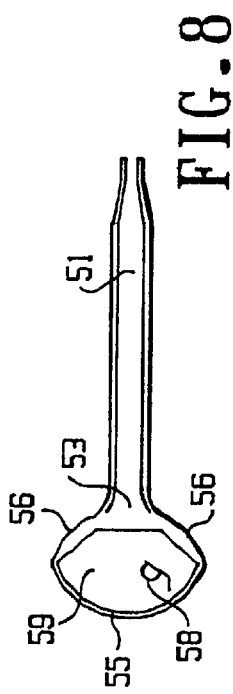
FIG. 4
FIG. 5
FIG. 6
FIG. 7
FIG. 8

DENTAL OSCILLATING CLEANING IMPLEMENT AND METHOD OF USING SAME

This application is a C-I-P of application, Ser. No. 09/240,857, filed Feb. 1, 1999, now abandoned.

FIELD OF INVENTION

The present invention is concerned with an implement adapted for use in prophylaxis and periodontal treatments. In particularly, the present invention relates to a dental oscillating device, and to a method of using it.

BACKGROUND OF THE INVENTION

One type of dental cleaning implement now widely in use in prophylaxis treatments, periodontia, and other areas of operative dentistry, includes a handpiece having an oscillating drive and a metal tip which is used in cooperation with a water spray for dislodging calculus and stain.

The oscillating drive is operated at ultrasonic frequencies to produce extremely rapid microscopic strokes that are transmitted to the metal tip. At the same time water spray is applied to cool the region and flush away the dislodged calculus, soft tissue, debris and stains. An example of such cleaning implement is the Dentsply/Cavitron®, Model 3000 manufactured by the Cavitron Division of CooperCare Inc., Palo Alto, USA.

Another type of dental cleaning implement is described in my prior patent U.S. Pat. No. 5,393,229. The implement described in that patent, includes an electrical oscillating drive for oscillating the handpiece of the implement at a relatively high frequency, a head with a toothpick and a water spray nozzle for cooling the toothpick from the heat dissipated due to the oscillations. Due to the fact that the oscillating drive operates at a relatively high frequency, considerable amount of heat is discharged at the user/patient treated area, such as the gums, which normally results in a very unpleasant feeling. To overcome this problem, U.S. Pat. No. 5,393,229 discloses the use of a water spray nozzle that is used to cool the tip of the implement as well as the treated area.

U.S. Pat. No. 5,593,304 describes another type of dental cleaning implement. This implement comprises a head that includes one pair of nozzles, connectable to a source of liquid, a gas and/or powder. A manual fluid selecting device allows the user to select the liquid, and/or gas and/or powder for discharge at the tip area.

SUMMARY OF INVENTION

It is an object of the present invention to provide an efficient and comfortable-to-use implement that is adapted for dental cleaning.

It is another object of the present invention to provide a method of dental cleaning.

Other objects of the invention will become apparent as the description of the invention proceeds.

According to the present invention, there is provided a dental cleaning implement comprising: a handpiece graspable at one end by a user, an oscillating drive within the handpiece adapted to provide oscillations of up to 15,000 stokes per second, a head located at the opposite end of the handpiece which includes a coupler for releasably attaching a toothpick, an interdental toothbrush or a tongue scraper thereto, and optionally a selector for varying the frequency of oscillation. By a preferred embodiment of the invention, the oscillating drive wifthin the handpiece is adapted to provide oscillations in the range of 1 to about 5,000 strokes per second.

In accordance with the present invention, the toothpick to be releasably attached to the coupler can be made from wood, plastic, metal with or without a coating of plastic material, nylon, composite material or any other material which is known per se in the art.

The oscillating drive of the present invention can be operated electrically, electromagnetically, mechanically, piezoelectrically, pneumatically, or by any other method which is known per se in the art.

In accordance with an embodiment of the invention, the toothpick, the interdental toothbrush stem or the tongue scraper stem is releasably attached by the coupler so as to form about 90° with the axis of the implement's head.

An example of a coupler of the invention is a coupler that comprises a screw mounted on the head for attaching the toothpick, the interdental toothbrush or the tongue scraper thereto. However, it should be understood that any other releasably attaching coupler that is known per se in the art and which can be used with such an implement, is also, encompassed by the present invention.

In accordance with another embodiment of the invention, the releasably attaching coupler includes a stem comprising a transverse bore for receiving a toothpick, an interdental toothbrush or a tongue scraper, and a sleeve moveable with respect to the stem to clamp the toothpick, the interdental toothbrush stalk or the tongue scraper stalk within the transverse bore. The head of the implement according to this embodiment may be coaxial with the stem. By this embodiment, the angle formed between the axis of the toothpick and the axis of the stem is preferably in the range of from about 10° to about 25°, most preferably from about 13° to about 16°, with the axis of the head.

In accordance with yet another embodiment of the invention, there is provided an implement wherein the releasably attaching coupler includes a stem that is screwable to the head to clamp the toothpick, the interdental toothbrush stalk or the tongue scraper stalk to the head. Preferably, in such embodiment the head is coaxial with the stem, and by another aspect of this embodiment the axis of the toothpick, the interdental toothbrush or tongue scraper forms an angle of from about 10° to about 20°, most preferably from about 13° to about 16° with the axis of the head.

In accordance with a further embodiment of the present invention there is provided an implement wherein the toothpick may be attached by the releasably attaching coupler substantially coaxially with respect to the implement head. By this embodiment, the releasably attaching coupler comprises a socket formed at the end of the head for snuggly receiving one end of the toothpick.

In accordance with still another embodiment of the invention, there is provided a kit comprising a dental cleaning implement of the invention and at least one member of the group consisting of a toothpick, interdental toothbrush and a tongue scraper adapted to be releasably attached by the coupler of the implement. Toothpicks within the scope of this embodiment can be made from wood, plastic, metal, with or without a coating of plastic material, nylon, composite material or any other material, known per se in the art. Furthermore, the, at least one toothpick may be coated, soaked or impregnated with various compositions suitable for dental cleaning, tergenetics or diagnostic purposes. In accordance with this embodiment, the toothpick to be used is coated, soaked or impregnated with one or more of the following reagents; a topical anesthetic agent such as ethyl aminobenzoate or benzoalkonium chloride; olive oil or other oil which may be helpful in enhancing the removal of bacterial plaque from the teeth, from the space between the teeth and from the space between the teeth and gums; a fluoride which may be helpful in increasing the resistance of teeth to decay; a color-changing pH indicator such as phenol phthalein, which may be useful in indicating the acidic or basic condition in the gum for determining the subject's gums health conditions, an antibiotic agent, such as tetracycline; an anti-inflammatory agent such as indometacine; a sensitivity-reducing agent,'such as amine fluoride; an anti-calculus agent such as anti-formic/citric acid or pyrophosphate, or any other composition known per se in the art for such or similar use.

According to another embodiment of the invention, the implement further comprises a drive that provides the toothpick being oscillated with a movement relative to the longitudinal axis of the toothpick. Typical such movement may be forth and back movement, annular movement or any other suitable type of movement or a combination of movements that will enhance the performance of the implement in the dental cleaning.

As was described hereinbefore, the implement of the present invention can be used for cleaning the space between the teeth as well as the space between the teeth and the gums, the suclus. Preferably this implement is operated at a frequency in the range of 1 to about 5,000 Hz. Still more preferably, when operating the implement of the invention at such frequencies no cooling means are required. It may also be used for cleaning implants, porcelain crowns, bridges and the like.

By another aspect of the invention, there is provided a method of dental cleaning which comprises:

(i) grasping a dental implement which comprises a handpiece graspable at one end, an oscillating drive within the handpiece, a head located at the opposite end of the handpiece which includes a coupler for releasably attaching a toothpick or an interdental toothbrush thereto, by the graspable end of the handpiece;

(ii) attaching a toothpick or interdental toothbrush to the head of the dental implement by the coupler thereof;

(iii) operating the oscillating drive within the handpiece; and (iv) applying the toothpick or the interdental toothbrush to the space between the teeth and/or to the space between the gums, while the toothpick or the interdental is oscillated at a frequency in the range of 1 to about 15,000 strokes per second.

According to a preferred embodiment of the invention, the method of dental cleaning further comprises applying a liquid or paste onto the toothpick or interdental brush.

Some important advantages were found while using a dental implement of the present invention. A dental cleaning implement so constructed can be used not only for cleaning the space between the teeth, but also the sulcus, the space existing between the teeth and the gums. Such a cleaning implement allows a highly efficient cleaning of the teeth by the patient himself. The cleaning is not painful, and presents a low risk of self injury, thereby obviating the need to make frequent visits to the dentist for this purpose.

As previously explained, the dental cleaning implement of the invention may be used either with a releasably attached toothpick thereto or alternatively, with releasably attached interdental toothbrush thereto, allowing efficient brushing between teeth. In addition, the dental cleaning implement does not require any cooling means, and subgingival cleaning is carried out without the use of a cooling fluid. Hardened plaque can be removed without the need for water cooling.

Further features and advantages of the invention will be apparent from the description below.

BRIEF DESCRIPTION OF THE DRAWINGS

The invention is herein described, by way of example only, with reference to the accompanying drawings, wherein:

FIG. 4 is an enlarged fragmentary view illustrating the head of the dental implement of FIG. 3;

FIG. 5 illustrates a head of a dental implement of the invention adapted to receive an interdental toothbrush, and a spiral interdental toothbrush attached thereto;

FIG. 6 illustrates an exploded view of another type of a dental cleaning implement of the present invention and a toothpick attached thereto; and FIG. 7 is an enlarged fragmentary view illustrating the head of the dental implement of FIG. 6.

FIG. 8 shows a removable tongue scraper for use with the dental cleaning implement.

DESCRIPTION OF PREFERRED EMBODIMENTS

The invention will now be illustrated by the following non-limiting examples demonstrating a number of embodiments of the dental implement of the invention.

Figure 1:
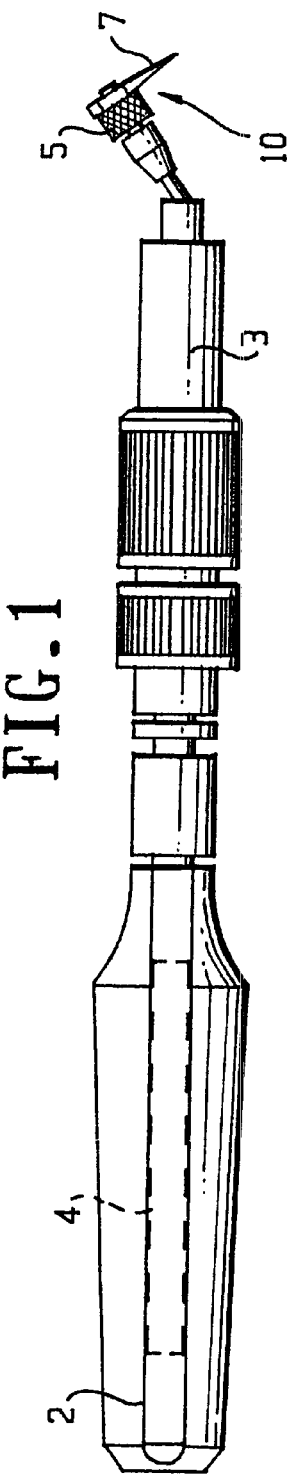
FIG. 1 illustrates one type of the dental cleaning implement of the present invention and a toothpick attached thereto.

The dental cleaning implement 1 illustrated in FIG. 1, comprises a handpiece 2 graspable at one end by a user, a stem 3 attached to the opposite end of handpiece 2 and head 10 attached to stem 3. Handpiece 2 comprises an oscillating drive 4, schematically shown in broken lines. Oscillating drive 4 provides oscillations to handpiece 2 at a frequency of up to 15,000 strokes per second, and preferably at the range of 1 to 5,000 strokes per second. As was previously explained, the oscillating drive 4 may be motivated by any one of the methods known per se in the art, among which electromagnetically, pneumatically, piezoelectrically, mechanically or by a magnetostrictive stack which converts electrical power supplied to the handpiece into mechanical oscillations at the required frequency. Head 10 comprises a coupler 5 for attaching the toothpick 7 thereto.

Figure 2A:
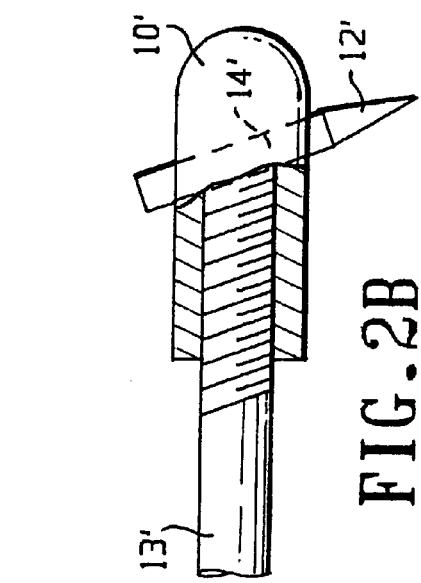
FIG. 2a is an enlarged fragmentary view illustrating the head of the dental implement of FIG. 1.
Figure 2B:
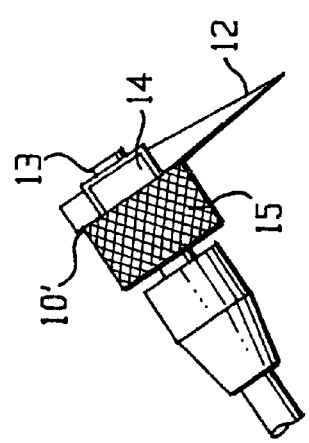
FIG. 2b is an enlarged fragmentary view illustrating another head of a dental implement of the invention.

An enlarged view of optional heads 10' and 10" for the implement shown in FIG. 1 are illustrated in FIGS. 2a and 2b. In these two Figures, stem 13 and 13' comprise transverse bores 14 and 14', respectively, extending therethrough for receiving toothpicks 12 and 12', respectively. Head 10' illustrated in FIG. 2a, further comprises a sleeve 15 which is moveable with respect to the stem 13 in one direction to clamp toothpick 12 within bore 14, and in the opposite direction to release the toothpick from the bore and thereby permit its removal and replacement by another toothpick. Toothpick. 12' shown in FIG. 2b is clamped to the head 10" by the stem of the handpiece (not shown in this FIG.). In the example illustrated in FIG. 1, the axis of the head 10 (or 10' as illustrated in FIG. 2a) is at an angle of about 15° with the axis of handpiece 2, and the axis of the toothpick 7 is substantially perpendicular to the axis of head 10. In the variation illustrated in FIG. 2b, head 10" is coaxial with the axis of the handpiece (not shown in this Fig,) and the axis of the toothpick 12' is at an angle of about 20° with the axis of head 10". In the example illustrated FIG. 2a sleeve 15 is retained in either its clamping position or releasing position by a friction fit with respect to stem 13. It will he appreciated however, that other types of retainers could be used, e.g. screw threads, ball-and-detent retainers, and the like.

FIG., 3 illustrates a variation of the implement of the invention, wherein the axis of head 20, is inclined with respect to the axis of the handpiece 22, and toothpick 26 is coaxial with the axis of head 20. An enlarged view of head 20 is presented in FIG. 4 wherein head 20' comprises a socket 34 that frictionally receives one end of toothpick 32.

Figure 3:
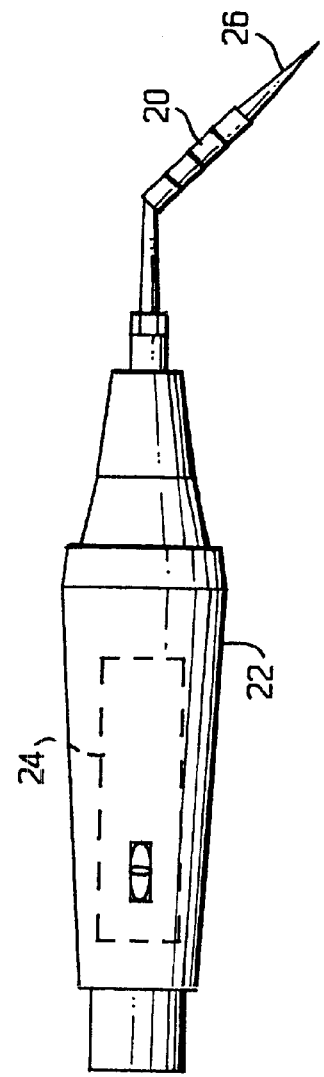
FIG. 3 illustrates another type of the dental cleaning implement of the present invention and a toothpick attached thereto.

The cleaning implement illustrated in FIGS. 3 and 4 is otherwise of the same construction as described above with respect to FIGS. 1 and 2. The toothpicks presented in all these figures may be made of wood, plastic, metal with or without a coating of plastic material, nylon, composite material or any other material that is known per se in the art.

As was previously explained and in accordance with a preferred embodiment of the invention, the toothpick to be used may be coated, soaked or impregnated with one or more reagents. Such reagents may be: a topical anesthetic agent such as ethyl aminobenzoate or benzoalkonium chloride; olive oil or other oil which may be helpful in enhancing the removal of bacterial plaque from the teeth, from the space between the teeth and from the space between the teeth and gums; a fluoride which maybe helpful in increasing the resistance of teeth to decay; a color-changing pH indicator such as phenol phthalein, which may be useful in indicating the acidic or basic condition in the gum for determining the subject's gums health conditions; an antibiotic agent, such as tetracycline; an anti-inflammatory agent such as indometacine; a sensitivity-reducing agent such as amine fluoride; an anti-calculus agent such as anti-formic/citric acid or pyrophosphate, or any other composition known per se in the:art for such or similar use. Also, by using toothpicks coated, soaked or impregnated with one or more of the reagents described above, the efficiency of the teeth treatment can be further enhanced, and if required the toothpick can be used for diagnosing the medical dental condition of the patient. FIG. 5 illustrates the head of a dental implement similar to that described above for the implements presented in FIGS. 1 and 3. By the variation illustrated in this Figure, instead of attaching a toothpick to head 38, a spiral toothbrush 35 is attached by the coupler thereto, allowing the dental implement to be used for brushing the teeth. In this Fig., the implement stem is designated by 39, while the toothbrush stem by 36. Stem 36 is attached to head 38 in the same manner as for example toothpick 12 in FIG. 2a. As illustrated in FIG. 5, toothbrush 35 comprises a conical array of bristles.

In FIG. 6, which presents another variation of the dental implement of the invention, toothpick 42 is clamped to head 45 by a screw 41, which is screwed to the head by using a screw driver 43 adapted for that use. In this example, screw 41, is coaxial with stem 47. The transverse bore 49 that receives the toothpick is at about 15° with the axis of head 45. To enhance the efficacy of the implement, a container 46 for a liquid or paste, can be attached or inserted to handpiece 48. The discharge of the material from the container can be done by applying pressure thereon, by the vibrations provided by the implement drive or by any other suitable way. Container 46, may preferably be designed with an egress means allowing the material to be released on toothpick 42.

FIG. 7, which is an enlarged view of the head of the implement illustrated in FIG. 6, presents a variation wherein the axis of head 45' is coaxial with the axis of the handpiece (not shown in FIG. 7) and the axis of toothpick 42' is at an angle of about 20', with the axis of head 45'.

Referring now to FIG. 8, there is provided a removable device having a tongue scraper end 53 and stem 51 that can be removably attached to the implement of the present invention (not shown in this Figure). An arcuate blade member 55 is disposed and attached to the scraper end of the handle by support means 56, which in this Figure are simply a pair of support beams. The arcuate member has a concave 57 and a convex 58 surface and is supported by the support means such that the concave surface faces the scraper end of the elongate stem. In addition or alternatively, either one of surfaces 57 or 58 is further provided with bristles. The support means and arcuate blade member together define an aperture 59 between the arcuate blade member and the scraper end of the stem.

One of the major advantages achieved by this embodiment of FIG. 8 is the following. Normally, every time a human tongue is touched, the tongue shrinks and the upper surface of its rear part that is basically convex, is turned into a concave shape. This phenomenon results in that the tongue can be cleaned much less efficiently. The result vibrations created by the implement encompassed by this embodiment is the relaxation of the tongue mussels, which in turn substantially increases the effectiveness of the cleaning.

In the case that the frequency range of the dental implement is less than 5 KHz, cooling means are not required, and sub-gingival cleaning is carried out without the use of a cooling fluid allowing the removal of hardened plaque without the need for water cooling.

While the invention has been described with respect to several preferred embodiments, it will be appreciated that these are set forth merely for the purpose of example, and that many other variations, modifications and applications of the invention which arc encompassed thereby, may be made.

What is claimed is:

1. A method of sub-gingival cleaning comprising:

providing a dental implement which comprises a handpiece graspable at one end, an oscillating drive within the handpiece, a head located at the opposite end of the handpiece which includes a coupler for releasably attaching a toothpick thereto, said oscillating drive provides oscillations to said head at a frequency of from 1,000 to about 5000 strokes per second;

attaching a toothpick to the head of the dental implement by the coupler thereof;

operating the oscillating drive within the handpiece; and applying the toothpick to the space between the teeth and the gums, while the toothpick is oscillated, and removing hardened plaque from the sulcus without applying water cooling.

2. The method according to claim 1, further comprising applying a liquid or paste onto said toothpick for using same in dental cleaning.

3. The method of claim 1, wherein said sub-gingival cleaning is carried out without the use of a cooling fluid.

4. The method of claim 1, wherein said frequency is below about 5,000 strokes per second.

* * * * *